(12) United States Patent
Kang et al.

(10) Patent No.: US 9,902,753 B2
(45) Date of Patent: Feb. 27, 2018

(54) METHOD OF PURIFYING A LONG-ACTING HUMAN GROWTH HORMONE

(71) Applicants: CJ HEALTHCARE CORPORATION, Seoul (KR); ALTEOGEN, INC, Daejeon (KR)

(72) Inventors: Gil Bu Kang, Busan (KR); Chung Min Lee, Gyeonggi-do (KR); Jee Won Ahn, Seoul (KR); Dong Eok Lee, Seoul (KR); Chang Bong Jun, Seoul (KR); Won Jeong Lee, Seoul (KR); Sung Yoo Cho, Gyeonggi-do (KR); Chi Hye Park, Gyeonggi-do (KR); Ki Wan Kim, Seoul (KR); Yoon Jung Lee, Gyeonggi-do (KR); Ji Hyun Moon, Seoul (KR); Hoo Keun Oh, Seoul (KR); Young Joon Park, Seoul (KR); Sang Hyun Lee, Seoul (KR); Hyoung Taek Lim, Incheon (KR); Soon Jae Park, Daejeon (KR); Hye Shin Chung, Daejeon (KR); Sang Mee Lee, Daejeon (KR)

(73) Assignees: CJ HEALTHCARE CORPORATION, Seoul (KR); ALTEOGEN, INC, Daejeon (KR)

( * ) Notice: Subject to any disclaimer, the term of this patent is extended or adjusted under 35 U.S.C. 154(b) by 122 days.

(21) Appl. No.: 14/406,192

(22) PCT Filed: Jun. 5, 2013

(86) PCT No.: PCT/KR2013/004985
§ 371 (c)(1),
(2) Date: Dec. 5, 2014

(87) PCT Pub. No.: WO2013/183948
PCT Pub. Date: Dec. 12, 2013

(65) Prior Publication Data
US 2015/0126715 A1 May 7, 2015

(30) Foreign Application Priority Data

Jun. 5, 2012 (KR) .......................... 10-2012-0060641
May 31, 2013 (KR) .......................... 10-2013-0063053

(51) Int. Cl.
| | | |
|---|---|---|
| C07K 1/22 | (2006.01) |
| C07K 1/16 | (2006.01) |
| C07K 14/61 | (2006.01) |
| C07K 19/00 | (2006.01) |
| C07K 1/14 | (2006.01) |
| C07K 14/81 | (2006.01) |

(52) U.S. Cl.
CPC .................. C07K 1/16 (2013.01); C07K 1/14 (2013.01); C07K 14/61 (2013.01); C07K 14/8125 (2013.01); C07K 19/00 (2013.01); C07K 2319/00 (2013.01)

(58) Field of Classification Search
None
See application file for complete search history.

(56) References Cited

U.S. PATENT DOCUMENTS

| 8,178,108 | B2 * | 5/2012 | Buechler ................ C07K 14/61 |
| | | | 424/123 |
| 9,051,395 | B2 * | 6/2015 | Park .................... A61K 38/1709 |
| 2011/0072526 | A1 | 3/2011 | Melo et al. |
| 2011/0288005 | A1 | 11/2011 | Silverman et al. |
| 2012/0094356 | A1 | 4/2012 | Chung et al. |

FOREIGN PATENT DOCUMENTS

| CN | 102439044 A | 5/2012 |
| CN | 103827141 A | 5/2014 |
| EP | 0734393 B1 | 4/1999 |

(Continued)

OTHER PUBLICATIONS

"Resistance to Proteolysis of Antibody Ligands Modified with Polyethylene Glycol", Journal of Fermentation and Bioengineering vol. 71, No. 2, 137-139. 1991 by Eizo Sada et al. at Chemical Engineering Department, Kyoto University.

"Optimization of Inclusion Body Solubilization and Renaturation of Recombinant Human Growth Hormone from *Escherichia coli*", Protein Expression and Purification 18, 182-192 (2000) by Ashok K. Patra et al.

"Development and characterization of novel erythropoiesis stimulating protein (NESP)", British Journal of Cancer (2001) 84 (Supplement 1), 3-10 by JC Egrie and JK Browne.

(Continued)

*Primary Examiner* — Christine J Saoud
(74) *Attorney, Agent, or Firm* — Masuvalley & Partners (57) ABSTRACT

The present invention relates to a long-acting human growth hormone NexP-hGH protein and its production method. More specifically, it relates to a specific isoform of long-acting human growth hormone NexP-hGH protein in which human growth hormone is fused with a highly glycosylated alpha-1 antitrypsin mutant whereby long-acting properties in vivo are increased. The present invention also relates to a high-purity purification method for NexP-hGH, which includes the steps of: (a) carrying out anion-exchange resin chromatography on a biological emulsion comprising NexP-hGH in which human growth hormone is fused with an alpha-1 antitrypsin mutant; (b) carrying out hydrophobic resin chromatography on the biological emulsion comprising NexP-hGH, or on the eluate produced in step (a); and (c) carrying out affinity chromatography, entailing packing with a resin to which anti-alpha-1 antitrypsin antibody fragments are attached, on the biological emulsion comprising NexP-hGH and on the eluate produced in step (a) or step (b).

10 Claims, 8 Drawing Sheets

(56) References Cited

FOREIGN PATENT DOCUMENTS

KR       930009336 B1    9/1993
KR   1020100037496 A   11/2010

OTHER PUBLICATIONS

"Haematopoietic growth factors / Glycosylated vs non-glycosylated granulocyte colony-stimulating factor (G-CSF)—results of a prospective randomised monocentre study", Bone Marrow Transplantation (2001) 28, 259-264 by H Bonig1, S Silbermann et al.

* cited by examiner

FIG. 1

1. Total eluated long-acting human growth hormone

2. Isoform 1: long-acting human growth hormone eluated with 100mM $MgCl_2$/Tris buffer solution (pH 7.4)

3. Isoform 2: long-acting human growth hormone eluated with 200mM $MgCl_2$/Tris buffer solution (pH 7.4)

4. Isoform 3: long-acting human growth hormone eluated with 300mM $MgCl_2$/Tris buffer solution (pH 7.4)

FIG. 2

1. Total eluated long-acting human growth hormone

2. Isoform 1: long-acting human growth hormone eluated with 100mM $MgCl_2$/Tris buffer solution (pH 7.4)

3. Isoform 2: long-acting human growth hormone eluated with 200mM $MgCl_2$/Tris buffer solution (pH 7.4)

4. Isoform 3: long-acting human growth hormone eluated with 300mM $MgCl_2$/Tris buffer solution (pH 7.4)

| Group /substance for administration /dose for administration /administration interval | | Day 1 | | | Day 14 | | |
|---|---|---|---|---|---|---|---|
| | | Body Length (cm) | Tail Length (cm) | Total Length (cm) | Body Length (cm) | Tail Length (cm) | Total Length (cm) |
| G1 (Intact) PBS 0 QD | Mean(g) | 13.7 | 11.8 | 25.5 | 17.2 | 14.6 | 31.8 |
| | S.D. | 0.3 | 0.8 | 0.9 | 0.3 | 0.5 | 0.6 |
| | increase rate(%) | – | – | – | 25.6 | 23.2 | 24.5 |
| G2 PBS 0 QD | Mean(g) | 13.8 | 11.6 | 25.4 | 14.2 | 11.3 | 25.5 |
| | S.D. | 0.4 | 0.2 | 0.2 | 0.3 | 0.4 | 0.6 |
| | increase rate(%) | – | – | – | 2.9 | – | 0.4 |
| G3 Eutropin 0.1 mg/kg QD | Mean(g) | 14.3 | 11.4 | 25.7 | 14.9## | 11.5 | 26.4 |
| | S.D. | 0.4 | 0.7 | 1.0 | 0.4 | 0.6 | 0.9 |
| | increase rate(%) | – | – | – | 4.7 | 0.7 | 2.9 |
| | P value (vs.G2) | – | – | – | 0.006 | 0.568 | 0.090 |
| G4 Declage 0.2 mg/kg Q2D | Mean(g) | 14.2 | 11.7 | 25.8 | 14.8# | 12.0* | 26.8## |
| | S.D. | 0.5 | 0.4 | 0.6 | 0.4 | 0.3 | 0.6 |
| | increase rate(%) | – | – | – | 4.1 | 2.9 | 3.5 |
| | P value (vs.G2) | – | – | – | 0.033 | 0.014 | 0.008 |
| | P value (vs.G3) | – | – | – | 0.485 | 0.114 | 0.476 |
| G5 CJ-40002 isoform 1 0.6 mg/kg Q2D | Mean(g) | 14.0 | 11.8 | 26.0 | 14.9## | 12.4##,* | 27.3## |
| | S.D. | 0.4 | 0.4 | 0.6 | 0.2 | 0.6 | 0.5 |
| | increase rate(%) | – | – | – | 6.5 | 4.9 | 3.1 |
| | P value (vs.G2) | – | – | – | 0.001 | 0.007 | 0.000 |
| | P value (vs.G3) | – | – | – | 1.000 | 0.026 | 0.059 |
| G6 CJ-40002 isoform 2 0.6 mg/kg Q2D | Mean(g) | 14.0 | 11.7 | 25.8 | 15.1## | 12.2# | 27.3# |
| | S.D. | 0.3 | 0.5 | 0.7 | 0.2 | 0.7 | 0.8 |
| | increase rate(%) | – | – | – | 7.7 | 4.3 | 5.5 |
| | P value (vs.G2) | – | – | – | 0.000 | 0.038 | 0.003 |
| | P value (vs.G3) | – | – | – | 0.363 | 0.110 | 0.117 |
| G7 CJ-40002 isoform 3 0.6 mg/kg Q2D | Mean(g) | 13.9 | 11.9 | 25.8 | 14.7 | 11.8 | 26.5 |
| | S.D. | 0.2 | 0.7 | 0.8 | 0.4 | 0.4 | 0.7 |
| | increase rate(%) | – | – | – | 5.4 | – | 2.6 |
| | P value (vs.G1) | – | – | – | 0.058 | 0.304 | 0.864 |
| | P value (vs.G2) | – | – | – | 0.296 | 0.448 | 0.527 |

P<0.05 vs PBS; ##P<0.01 vs PBS (Student's t test)
*P<0.05 vs Eutropin; **P<0.01 vs Eutropin (Student's t test)

```
SEQUENCE LISTING

<160> NUMBER OF SEQ ID NOS: 1

<210> SEQ ID NO 1
<211> LENGTH: 394
<212> TYPE: PRT
<213> ORGANISM: Homo sapiens

<400> SEQUENCE: 1

Glu Asp Pro Gln Gly Asp Ala Ala Gln Lys Thr Asp Thr Ser His His
 1               5                  10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
```

-continued

```
                245                 250                 255
Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Asp Gln Asn Thr Lys Ser Pro Leu Phe
    370                 375                 380

Met Gly Lys Val Val Asn Pro Thr Gln Lys
385                 390
```

METHOD OF PURIFYING A LONG-ACTING HUMAN GROWTH HORMONE

CROSS-REFERENCE TO RELATED APPLICATIONS

This application is the national phase entry under 35 U.S.C. § 371 of International Application No. PCT/KR2013/004985, filed on Jun. 5, 2013, which claims priority under 35 U.S.C. § 119 to Korean Patent Application No. 10-2012-0060641, filed on Jun. 5, 2012 and Korean Patent Application No. 10-2013-0063053, filed on May 31, 2013, the contents of which are hereby incorporated by reference in their entirety for all purposes.

TECHNICAL FIELD

The present invention relates to a long-acting human growth hormone NexP-hGH protein, which is highly glycosylated and highly long-acting in vivo, and a method for preparing the same. More particularly, the present invention relates to a specific isoform of long acting human growth hormone NexP-hGH protein in which human growth hormone is fused with a highly glycosylated alpha-1 antitrypsin mutant and a method for preparing the same.

The method for preparing the long-acting human growth hormone also relates to a method for purification of NexP-hGH in high purity, specifically, including: (a) applying a biological fluid comprising a long-acting human growth hormone NexP-hGH protein, wherein human growth hormone is fused with an alpha-1 antitrypsin mutant, to anion-exchange resin chromatography; (b) applying a biological fluid comprising the NexP-hGH or an eluate produced in step (a) to hydrophobic resin chromatography; and (c) applying a biological fluid comprising the long-acting human growth hormone NexP-hGH or an eluate produced in step (a) or step (b) to an affinity chromatography column filled with resin to which anti-alpha-1 antitrypsin antibody fragments are attached.

BACKGROUND OF THE INVENTION

Generally, a natural type human growth hormone (hGH) consists of 191 amino acids having a molecular weight of about 21,500 dalton. The human growth hormone is secreted from the anterior pituitary and promotes the growth of bones and cartilages in vivo. Deficiency in growth hormone may cause short stature, increase the risk of cardiovascular diseases, decrease muscle and bone density, etc.

For the treatment of growth hormone deficiency, growth hormones derived from human pituitary gland or produced via genetic engineering technology, have been used since the late 1950s, and the global human growth hormone market had already reached about 3 trillion Korean Won in 2009. However, the above growth hormones had a drawback in that they had to be administered daily via subcutaneous injection and thus there has been a need for the improvement and increase of patient compliance. To comply with the request, long-acting human growth hormone has been developed, and in an effort to improve its long-acting property, sustained-release formulations, and engineering such as fusion to proteins or saccharides, glycotechnology, etc., have been employed. For example, Genentech Inc. released Nutropin Depot® as the first sustained-release human growth hormone product, and LG Life Sciences LTD. (Korea) released Declage Inj.® (KR Pat. Nos. 10-0236771 and 10-0329336) in 2007. Nevertheless, the sustained-release treatments still have problems, in that they cause unwanted immune responses in the body, induce pain due to the use of rather thick syringe needles, and have low production yield. In particular, Nutropin Depot® was withdrawn from the market due to its low efficacy compared to that of other first-generation products.

In order to improve the sustained activity of proteins other than sustained-release formulations, methods such as fusion to polyethylene glycol as a polymer (Sada et al., *J. Ferment Bioeng* 71, 137-139, 1991), glycoengineering (U.S. Pat. No. 7,217,689), and fusion to other proteins (WO93/15199) may be used to promote absorption, metabolism, and excretion in the body. However, the above methods have not been used as conventional half-life increase methods for various reasons, including low cost-effectiveness due to low production yield, induction of immune responses during long-term use, toxicity of chemical substances used during conjugation, etc. Accordingly, there has been a need for the development of a long-acting human growth hormone using a method of improving its long-acting property while minimizing the above-described problems. KR Patent No. 10-1183262 discloses the development of a long-acting human growth hormone protein in the form of a conjugate between a mutant of alpha-1 antitrypsin (A1AT) as a body protein and a human growth hormone attempting to improve half-life via protein size increase. Additionally, KR Patent Application Publication No. 10-2013-0029713 discloses a method of attempting to increase in vivo half life by adding N-glycan via at least one mutation on alpha-1 antitrypsin.

The alpha-1 antitrypsin (A1AT) mutant used by the present inventors is one where a particular amino acid is mutated in order to remove the intrinsic in vivo activity of the alpha-1 antitrypsin as a protease inhibitor while increasing its half-life. The protein sequence of alpha-1 antitrypsin which has its intrinsic activity as a protease inhibitor removed and a method of its preparation are disclosed in KR Patent Application Publication No. 10-2010-01165.

A long-acting human growth hormone is a fusion protein wherein a mutant of alpha-1 antitrypsin (A1AT) is fused to an N-terminus or C-terminus of a human growth hormone via genetic recombination, and is a material with improved half-life compared to those of first-generation human growth hormones. The long-acting human growth hormone was prepared so that it is expressed in CHO cells to be glycosylated while most of the first-generation human growth hormone drugs were manufactured in *E. coli*.

The purification of alpha-1 antitrypsin was conventionally carried out by selective precipitation of impurities using polyglycol and pH (EP Patent No. 0097274) and cation-exchange resin (EP Patent Nos. 96929430 and 95112630). Additionally, the first generation human growth hormones were generally prepared by over-expression in *E. coli* in the form of an inclusion body, followed by refolding and purification with anion-exchange resin (KR Patent Nos. 1998-0003752, and Patra A K, Mukhopadhyay R, Mukhija R, Krishnan A, Garg L C, Panda A K. (2000) 18, 182-192, 2000; *Protein Expr. Purif*).

Meanwhile, the long-acting human growth hormone NexP-hGH is a novel material having a molecular weight of about 70 to 90 kDa, which is different from the first generation human growth hormones or alpha-1 antitrypsin in terms of physicochemical properties such as molecular weight, isoelectric point, glycan patterns, etc., and long-acting human growth hormone with high purity could not be obtained by the same/similar purification methods as those used for the first generation human growth hormones or alpha-1 antitrypsin. Furthermore, the purification method of long-acting human growth hormone has never been disclosed in patents or scientific papers.

Under the circumstances, the present inventors, while endeavoring to find an efficient purification method for the long-acting human growth hormone, the high purity of which has not been deemed possible, have discovered that high purity long-acting human growth hormone can be obtained via anion-exchange resin, hydrophobic resin, resin to which antibody fragments are attached, etc.

Additionally, the degree of influence by the glycosylation level of proteins present in the body on half-life and efficacies varies depending on the type of the proteins, for example, the conventionally used protein drugs erythropoietin and granulocyte colony-stimulation factor (GCSF). The in vivo efficacies of erythropoietin (J C Egrie and J K Browne, British *J. of Cancer,* 84, 3-10, 2001), a protein present in the body, vary depending on its sialic acid content. Specifically, erythropoietin has a high correlation between sialic acid content and in vivo efficacies, and highly glycosylated glycan containing a predetermined rate or higher of sialic acid content for the exhibition of appropriate efficacies. In contrast, the efficacies of GCSF showed a difference of up to 25% in in vitro efficacies depending on the presence/absence of glycans, but there was no difference in in vivo efficacies (H Bonig et al. *Bone marrow transplantation,* 28, 259-264, 2001).

As such, the present inventors, while endeavoring to develop a human growth hormone exhibiting long-acting pharmacological activities both in in vitro and in vivo conditions while having a lower risk of immunogenicity, discovered that an isoform of the NexP-hGH protein having a specific pI, among the above proteins produced in animal cells, has an excellent in vivo long-acting effect and growth effect, and thereby completed the present invention.

Accordingly, the present invention has been made keeping in mind the above problems occurring in the prior art. An objective of the present invention is to provide a long-acting human growth hormone NexP-hGH protein produced in animal cells, wherein an alpha-1 antitrypsin mutant (NexP) is fused with human growth hormone (hGH), having an isoelectric point (pI) of 5.2 or less.

Another objective of the present invention is to provide a method for preparing a long-acting human growth hormone NexP-hGH protein, the method comprising: (a) applying a biological fluid comprising a long-acting human growth hormone NexP-hGH protein, wherein an alpha-1 antitrypsin mutant (NexP) is fused with human growth hormone (hGH), to an affinity chromatography column filled with resin to which anti-alpha-1 antitrypsin antibody fragments are attached; and (b) separating long-acting growth hormone NexP-hGH protein having an isoelectric point (pI) of 5.2 or less according to the difference in isoelectric point (pI). A further objective of the present invention is to provide a method of purifying high purity long-acting human growth hormone NexP-hGH.

SUMMARY OF THE INVENTION

In order to accomplish the above objectives, in an aspect, the present invention provides a long-acting human growth hormone NexP-hGH protein produced in animal cells, wherein an alpha-1 antitrypsin mutant (NexP) is fused with human growth hormone (hGH), having an isoelectric point (pI) of 5.2 or less.

In another aspect, the present invention provides a method of purifying a long-acting human growth hormone NexP-hGH, the method comprising: (a) applying a biological fluid comprising a long-acting human growth hormone NexP-hGH protein, wherein human growth hormone is fused with an alpha-1 antitrypsin mutant, to anion-exchange resin chromatography; (b) applying the biological fluid comprising the NexP-hGH or an eluate produced in step (a) to hydrophobic resin chromatography; and (c) applying the biological fluid comprising the long-acting human growth hormone NexP-hGH or an eluate produced in step (a) or step (b) to an affinity chromatography column filled with resin to which anti-alpha-1 antitrypsin antibody fragments are attached.

BRIEF DESCRIPTION OF THE DRAWINGS

The present disclosure is described in conjunction with the appended figures:

FIG. 8 shows pictures illustrating the difference in glycan pattern and isoelectric point of the long-acting human growth hormone separated and eluted out according to the concentration of $MgCl_2$. In the left picture, Lane 1: hydrophobic resin eluate; Lane 2: a long-acting human growth hormone NexP-hGH eluted with a 100 mM $MgCl_2$/Tris buffer solution (pH 7.4); Lane 3: a long-acting human growth hormone NexP-hGH eluted with a 200 mM $MgCl_2$/Tris buffer solution (pH 7.4); and Lane 4: a long-acting human growth hormone NexP-hGH eluted with a 300 mM $MgCl_2$/Tris buffer solution (pH 7.4). In the right picture, Lane 1: a long-acting human growth hormone NexP-hGH eluted with a 50 mM $MgCl_2$/Tris buffer solution (pH 7.4); Lane 2: a long-acting human growth hormone NexP-hGH eluted with a 100 mM $MgCl_2$/Tris buffer solution (pH 7.4); Lane 3: a long-acting human growth hormone NexP-hGH eluted with a 200 mM $MgCl_2$/Tris buffer solution (pH 7.4); and Lane 4: a long-acting human growth hormone NexP-hGH eluted with a 300 mM $MgCl_2$/Tris buffer solution (pH 7.4).

DETAILED DESCRIPTION OF INVENTION

As used herein, the term "human growth hormone (hGH)" refers to a peptide hormone which enables growth, cell reproduction or regeneration in humans. The human growth hormone may include any protein which can stimulate in vivo cell differentiation in physeal plate to promote growth without being limited to the present invention. The human growth hormone includes both naturally produced growth hormones and those produced by genetic engineering technology, but should not be limited thereto. Additionally, the information on the human growth hormone can be obtained from publicly available database such as GenBank provided by National Center for Biotechnology Information (NCBI) of the National Institute of Health (NIH), for example, a human growth hormone with Accession Number of AAA98618, etc., but is not limited thereto.

Since the human growth hormone can promote growth by stimulating cell differentiation of epiphyseal plate in vivo, it is regarded as an important therapeutic protein to be used in a subject having difficulty with in vivo synthesis or secretion. However, there has been a demand for the development of a long-acting human growth hormone with an increased half-life compared to the conventional growth hormones from the aspects of convenience in administration for patients and therapeutic effects. Accordingly, the present inventors developed an alpha-1 antitrypsin mutant, fused it to a human growth hormone, and expressed the resultant in animal cells thereby developing highly glycosylated human growth hormone NexP-hGH. The highly glycosylated human growth hormone NexP-hGH, being a protein produced in animal cells, has an isoelectric point (pI) of 5.2 or less. It has a higher degree of glycosylation than when pI exceeds 5.2, thereby enabling high long-acting property and efficacies.

As used herein, the term "long-acting human growth hormone" refers to a protein wherein human growth hormone (hGH) and alpha-1 antitrypsin mutant (NexP) are fused together, and may be interchangeably used with the term "NexP-hGH". The NexP is a term named by the present inventors, referring to a mutant of alpha-1 antitrypsin (A1AT), an in vivo protein, with an increased half-life by maintaining in vivo long-acting property, developed by the present inventors. The protein sequence of alpha-1 antitrypsin removed of its activity as a protease inhibitor and a method of its preparation, etc., are disclosed in KR Patent No. 10-1183262 and KR Patent Application Publication No. 10-2013-0029713, and the entire disclosure of KR Patent No. 10-1183262 or KR Patent Application Publication No. 10-2013-0029713 are used as references but are not limited thereto.

The alpha-1 antitrypsin is one of the proteins present in the blood of mammals having a molecular weight of about 50,000 Da, and is also named alpha-1 protease inhibitor. The alpha-1 antitrypsin extracted from blood has been approved by the FDA, and is already on the commercial market in the name Prolastin® as a therapeutic agent for treating emphysema. Prolastin® is conventionally administered at a dose of 60 mg/kg via intravenous injection at one weekly intervals, and it is a protein whose clinical safety in humans has been confirmed. Additionally, the functions and structures of the alpha-1 antitrypsin as a protease inhibitor are well known (Elliott, P. et al., JMB 275, 419-425, 1998). Additionally, the alpha-1 antitrypsin is present in more than 100 different kinds of alleles, and its phenotypes are classified into from 'A' to 'Z' according to its isoelectric focusing (IEF) type (Stoller et al., *The Lancet,* 365, 2225-2236, 2005). Among them, the most prevalent M type allele is a normal type which is classified again into subtypes such as M1 (Val213), M2, and M3 based on mutations in amino acid sequences. Accordingly, the alpha-1 antitrypsin used in the present invention is a specific subtype present in nature, and may have the same effect on other subtypes. The information on the alpha-1 antitrypsin can be obtained from publicly available database such as GenBank provided by NCBI of the NIH, for example, a wild type alpha-1 antitrypsin protein with Accession Number of AAH11991, but is not limited thereto. The sequence of the wild type alpha-1 antitrypsin protein is represented by SEQ ID NO:1.

The alpha-1 antitrypsin may be removed of its in vivo intrinsic activities by modifying at least one of its amino acid residues via site-directed mutagenesis, thereby increasing its half-life. By the above modification of amino acid residue(s), an N-glycosylated region of the alpha-1 antitrypsin is generated thereby minimizing the immunogenicity by amino acid substitution when injected into the body while neutralizing protease inhibitor activity of the alpha-1 antitrypsin, and dimer formation by free cysteines can be prevented. In particular, the mutations in at least one amino acid may be characterized by mutation on proline (P), the $357^{th}$ amino acid of the alpha-1 antitrypsin protein represented by SEQ ID NO: 1, which is P2 position in the alpha-1 antitrypsin protein, and more specifically, a conversion of the proline into asparagine (N). Additionally, the alpha-1 antitrypsin mutants may include a mutation on glutamine (Q), the $9^{th}$ amino acid of the alpha-1 antitrypsin protein represented by SEQ ID NO:1, into asparagine (N); a mutation on cysteine (C), $232^{nd}$ amino acid, into serine (S); or a mutation on serine (S), $359^{th}$ amino acid, into threonine (T), etc., and also the mutants may include at least one mutation described above, as well as a mutation on proline (P), the $357^{th}$ amino acid as the P2 position, into asparagine (N), but is not limited thereto.

The long-acting human growth hormone NexP-hGH is a protein wherein any of the above alpha-1 antitrypsin (A1AT) mutants is fused with an N-terminus or C-terminus of a human growth hormone via genetic recombination. In particular, the long-acting human growth hormone NexP-hGH may be a fusion protein (hGH-A1AT (Q9N, P357N)), wherein the alpha-1 antitrypsin protein mutant, where both the $9^{th}$ amino acid glutamine and the $357^{th}$ amino acid proline are mutated into asparagines, is fused with the N-terminus of the human growth hormone, but is not limited thereto.

As used herein, the term "highly glycosylated long-acting human growth hormone" refers to a long-acting human growth hormone protein in the form including an alpha-1 antitrypsin mutant and a human growth hormone, which has a higher degree of glycosylation than those of wild type proteins found in natural state, and has an isoelectric point of 5.2 or less.

In the present invention, it was confirmed that the long-acting activity became higher as the degree of glycosylation of the long-acting human growth hormone became higher. In particular, it was confirmed that, when the isoelectric point of the long-acting human growth hormone was 5.2 or less, the long-acting activity and drug activity in the body were extremely high both in vitro and in vivo.

The highly glycosylated long-acting human growth hormone has an isoelectric point of 5.2 or less, preferably in the range of from 3.5 to 5.2, but is not limited thereto. In detail, the glycosylated region is an amino acid residue or a region within a polypeptide where glycosylation such as the attachment of a carbohydrate structure can occur, for example, an N-glycosylated region or O-glycosylated region. The conserved N-glycosylated regions may be Asn-X-Ser or Asn-X-Thr wherein X is any amino acid, but is not limited thereto.

The highly glycosylated long-acting human growth hormone may be produced by culturing animal cells introduced with an expression vector comprising polynucleotide(s) encoding the long-acting human growth hormone.

As used herein, the term "animal cells" refers to cells which can express the long-acting human growth hormone of the present invention, and may not be particularly limited as long as they can cause glycosylation, for example, CHO cells, BHK cells, Vero cells, HeLa cells, MDCK cells, 293 cells and 3T3 cells, but not limited thereto.

Figure 1:
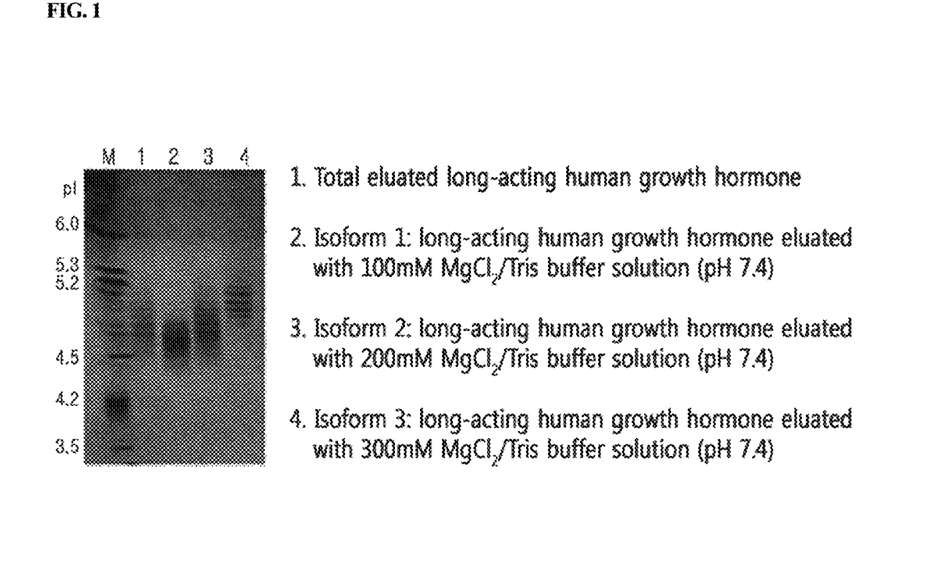
FIGS. 1 and 2 show the fractions of a long-acting human growth hormone according to the difference isoelectric point (pI).
Figure 2:
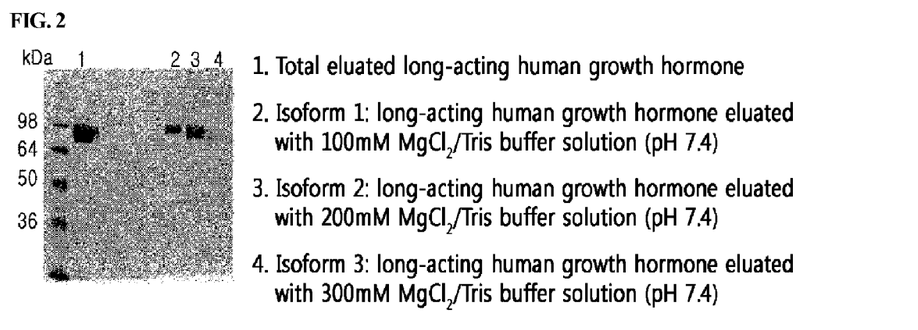
Figure 3:
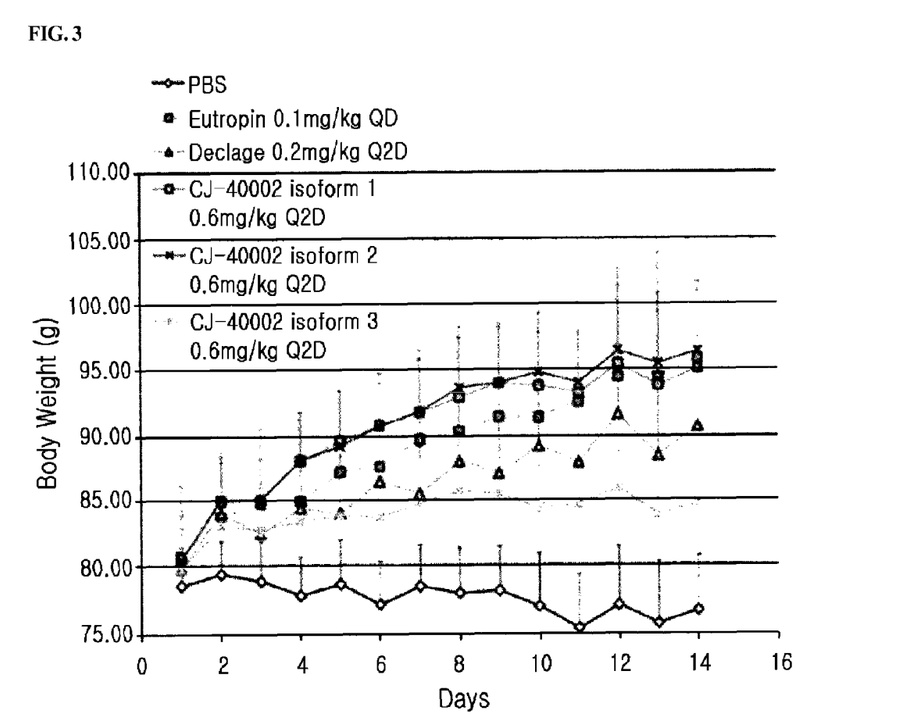
FIG. 3 shows a graph confirming the effect of isoforms 1 to 3 of the highly glycosylated long-acting human growth hormone of the present invention on body weight.

In an embodiment of the present invention, a human growth hormone protein fused to an alpha-1 antitrypsin wherein both the $9^{th}$ and the $357^{th}$ amino acids were substituted with asparagines was prepared, and a vector including a polynucleotide encoding the above protein was introduced into a CHO cell, thereby constructing a stable cell line (Example 1). Additionally, a NexP-hGH protein was obtained according to the difference in isoelectric point after sequentially performing anion-exchange resin chromatography, hydrophobic chromatography, and affinity chromatography wherein a column for the affinity chromatography is filled with resin to which anti-alpha-1 antitrypsin antibody fragments are attached. It was confirmed that isoform 1, which has the lowest pI among isoforms 1-3, has a higher degree of glycosylation than those of isoform 2 and isoform 3, and isoform 2, which has a lower pI than isoform 3, has a higher degree of glycosylation than isoform 3 (FIGS. 1 and 2). Additionally, from the pharmacodynamic point of view, it was confirmed that as the degree of glycosylation increased the long-acting human growth hormone of the present invention had an excellent pharmacodynamic property, and in particular, equivalent to or superior to that of positive control group (FIG. 3). Additionally, it was confirmed that isoform 2 and isoform 3 significantly increased the body length of experimental animals compared to those in the positive control group. That is, the highly glycosylated long-acting human growth hormone of the present invention exhibited a significantly higher validity compared to that of positive control group.

In another aspect of the present invention, there is provided a method for preparing a long-acting human growth hormone NexP-hGH protein including: (a) applying a biological fluid comprising a long-acting human growth hormone NexP-hGH protein, wherein an alpha-1 antitrypsin mutant (NexP) is fused with human growth hormone (hGH), to affinity chromatography column filled with resin to which anti-alpha-1 antitrypsin antibody fragments are attached; and (b) separating long-acting growth hormone NexP-hGH protein having an isoelectric point (pI) of 5.2 or less according to the difference in isoelectric point (pI). The alpha-1 antitrypsin mutant, human growth hormone, and the long-acting human growth hormone are the same as explained above.

Each step of the above preparation method may be explained in detail as follows:

First, step (a) relates to the application of a biological fluid comprising a long-acting human growth hormone NexP-hGH protein to affinity chromatography column filled with resin to which anti-alpha-1 antitrypsin antibody fragments are attached. The above step is a step for attaching NexP-hGH to a column via affinity between NexP and antibody fragments.

As used herein, the term "a biological fluid comprising a long-acting human growth hormone NexP-hGH" may refer to a cell culture supernatant of cells producing a long-acting human growth hormone NexP-hGH protein, a cell extract thereof, or a partially purified form thereof, but is not limited thereto. In particular, the biological fluid is preferably a cell culture supernatant or a cell culture extract of cells obtained by culturing animal cells introduced with an expression vector comprising a polynucleotide encoding the long-acting human growth hormone, or a cell extract thereof, but is not limited thereto.

As used herein, the term "partial purification" refers to a state indicating the presence of other proteins in addition to the protein having an intended pI value, after performing at least one fractionation procedure such as chromatography. The above partial purification procedure is not particularly limited regarding its type but may be, for example, a hydrophobic chromatography or anion-exchange resin chromatography, but is not limited thereto. The partial purification may be performed using at least one method selected from the group consisting of hydrophobic chromatography and anion-exchange resin chromatography, preferably, by applying the cell culture supernatant of cells producing the long-acting human growth hormone NexP-hGH protein or a cell extract thereof to anion-exchange resin chromatography or hydrophobic resin chromatography thereby producing an eluate therefrom, and more preferably, sequentially applying anion-exchange resin chromatography and hydrophobic resin chromatography and producing an eluate therefrom, but is not limited thereto.

Step (b) relates to separation of long-acting growth hormone NexP-hGH protein having an isoelectric point (pI) of 5.2 or less according to the difference in pI. In being separated from the resin to which the antibody fragments attached, the structural isoforms of the long-acting human growth hormone NexP-hGH having different glycan patterns and isoelectric points may be separated and eluted according to $MgCl_2$ concentration.

Accordingly, in step (b), in order to separate and elute the long-acting growth hormone with a pI of 5.2 or less, a Tris buffer solution comprising 0 to 1,000 mM $MgCl_2$, preferably 0 to 300 mM $MgCl_2$, more preferably 0 to 200 mM $MgCl_2$, and even more preferably 200 mM $MgCl_2$, may be applied, but is not limited thereto. In the Tris buffer solution for separation and elution, $MgCl_2$ may be optionally added or need not be added.

In a further aspect of the present invention, there is provided a method for preparing a long-acting human growth hormone. In an exemplary embodiment of the present invention, CHO cells transformed with the human growth hormone/alpha-1 antitrypsin mutant was cultured, and the supernatant of the cell culture was diafiltered via ultrafiltration using 20 mM sodium phosphate buffer solution. KR Patent Application No. 10-2010-0037496 is included as a reference in its entirety.

The preparation method is described in detail as follows: Step (a) relates to the application of a biological fluid comprising a long-acting human growth hormone NexP-hGH protein, wherein human growth hormone and an alpha-1 antitrypsin mutant are fused together, to an affinity chromatography column filled with resin to anion-exchange resin chromatography, preferably, the addition of a culture broth comprising a long-acting human growth hormone or a culture broth obtained by diafiltration of the culture broth with a buffer solution having pH 6 to 9 comprising 0 to 100 mM NaCl to equilibrated anion-exchange resin to be adsorbed thereto; wash the resultant with a buffer solution having pH 6 to 9 comprising 0 to 100 mM NaCl; and elute a fraction comprising the long-acting human growth hormone NexP-hGH with a buffer solution having pH 6 to 9 comprising 100 to 1,000 mM NaCl. Using the anion-exchange resin, the dye and nucleic acids such as DNA/RNA, in the cell culture can be removed, and the long-acting human growth hormone contained in the biological fluid can be concentrated.

As used herein, the term "anion-exchange resin chromatography" refers to conjugating negatively charged (or acidic) molecules to a positive charged support thereby separating the molecules according to the electric charge, and the homologues of the molecules (acidic, basic, and neutral) can be easily separated by the technology. The resin to be used in the anion-exchange chromatography of the present invention may include strong anion-exchange resin and weak anion-exchange resin without any limitation, for example, Sephadex®, Sepharose®, SOURCE®, Mono®, Mini® (GE healthcare), etc., and may also use resins whose functional groups are quaternary amine (Q), diethylaminoethyl (DEAE) and quaternary amino ethyl (QAE), although not limited thereto. Preferably, the functional groups of the resins may be Q or DEAE, more preferably Q Sepharose, which is a strong anion-exchange resin.

Anion-exchange resin chromatography may be performed via column chromatography or batch mode. For commercial manufacture, batch mode may be preferred. After washing the anion-exchange resin, elution is performed via a stepwise salt gradient or a continuous salt gradient. Any suitable stepwise salt gradient or continuous salt gradient may be used as long as they make it possible to separate impurities from the long-acting human growth hormone.

Additionally, the anion-exchange resin used in the anion-exchange resin chromatography of the present invention can be equilibrated using an aqueous buffer solution before adsorbing a culture broth thereto. When the culture broth is diluted with a buffer solution having a pH of 6 to 9 comprising 0 to 100 mM NaCl or concentrated or dialyzed before adsorbing the culture broth to the anion-exchange resin the purification efficiency can be much improved. The above may be achieved via diafiltration using ultrafiltration. The diafiltration makes it possible to remove low molecular weight materials having a molecular weight cut off (MWCO) of 30,000 or less in the culture broth (e.g., surfactants, dyes, small peptides, sugar components, etc.), and enhance column adsorption efficiency via buffer solution exchange using an equilibrium buffer solution for anion-exchange resin chromatography.

Meanwhile, the ultrafiltration enables to fractionate materials dissolved or dispersed in a liquid according to particle size, and in general, it enables to separate, concentrate and purify molecules or colloidal particles with a molecular weight of a few thousand to a few hundred thousand. The functions of an ultrafiltration membrane are indicated by MWCO, and the materials having a molecular weight greater than the MWCO of the membrane are excluded from filtration. Generally, MWCO is represented by the molecular weight of spherical proteins in which 90% can be excluded. The major functions of the ultrafiltration membrane are diafiltration, purification, and concentration.

The buffer solution to be used in the respective washing and elution steps include a sodium phosphate buffer solution, a potassium phosphate buffer solution, or a Tris buffer solution.

Figure 5:
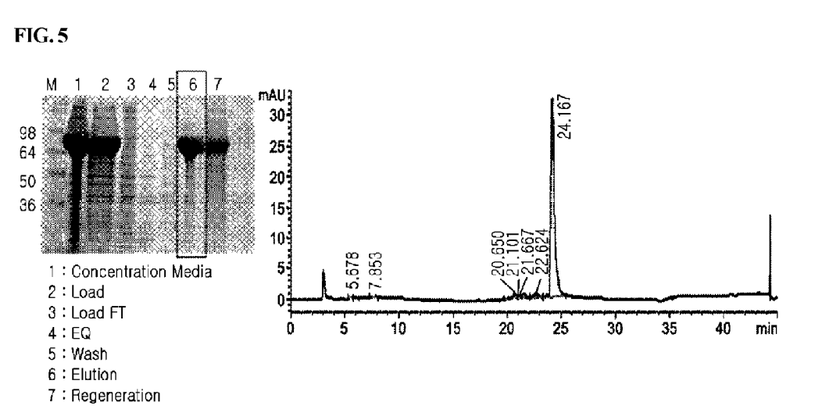
FIG. 5 shows a result of measuring the purity of a long-acting human growth hormone separated via anion-exchange resin chromatography and measured via SDS-PAGE and C4 HPLC analysis chromatography.

In an exemplary embodiment of the present invention, the culture broth obtained by the expression of the NexP-hGH, the long-acting human growth hormone, from the CHO cells, were diafiltered via ultrafiltration using a 20 mM sodium phosphate buffer solution (pH 8.0). The sample was then bound to XK-50 column filled with Q-Sepharose resin equilibrated using a 20 mM sodium phosphate buffer solution (pH 8.0) by loading at a flow rate of 20 mL/min, washed with three column volumes of 20 mM sodium phosphate buffer solution (pH 8.0) comprising 100 mM NaCl used as an elution solvent at a flow rate of 20 mL/min to remove impurities, and finally eluted the long-acting human growth hormone at about 85% purity (FIG. 5).

Step (b) may relate to the application of a culture broth comprising the long-acting human growth hormone NexP-hGH, or the eluate produced in step (a) into hydrophobic resin chromatography, wherein preferably, the solution recovered from the anion-exchange resin chromatography is added to equilibrated hydrophobic resin and adsorbed thereto, washed with a buffer solution having a pH of 6 to 8 comprising 1 to 3 M NaCl, to elute a fraction comprising the long-acting human growth hormone NexP-hGH with a buffer solution having a pH of 6 to 8 comprising 0 to 1 M NaCl. Hydrophobic resin enables to better remove cell-derived impurities unpurified from the anion-exchange resin. These results can be confirmed by comparison between the anion-exchange resin with about 80% purity and the hydrophobic resin in FIG. 6 at about 90% or higher purity.

As such, the constitution feature of the present invention performing step (b) after step (a) in purification, which differs from the conventional purification method, is based on the following discoveries on the combination of chromatographies:

(1) Because anion-exchange resin (about 10-20 mg NexP-hGH/resin 1 mL) has a higher binding capacity than the hydrophobic resin (about 6 mg NexP-hGH/resin 1 mL), anion-exchange resin is suitable for the first column, the primary goal of which is NexP-hGH capture in culture broth.

(2) In terms of process efficiency, upon completion of anion-exchange resin process, the eluate obtained from the antion-exchange resin can be directly applied to the hydrophobic resin process without going through with concentration/dialysis on the eluate obtained from anion-exchange resin.

When step (b), a hydrophobic resin process, is performed first, the eluate from hydrophobic resin should be concentrated/dialyzed with an equilibrium buffer for anion-exchange resin, and then proceeded with anion-exchange resin process thus having a disadvantage of requiring an additional process of concentration/dialysis.

(3) Furthermore, because anion-exchange resin is effective in removing dyes contained in the culture broth and removing DNA, the method of the present invention employing the anion-exchange resin in the first column can exhibit a superior purification result to that of the conventional purification method.

As used herein, the term "hydrophobic resin chromatography" refers to a chromatography being conducted in a gel having a hydrophobic, more suitably aromatic or aliphatic, ligand without charges conjugated to various kinds of matrices available in the market. The resin to be used as the above gel is preferred to have a relatively small bead size for high resolution, for example, Source (GE healthcare), Resource (GE healthcare), etc., but is not limited thereto. Preferably, the functional group of the resin to be served as a ligand may be phenyl, octyl, isopropyl, butyl, ethyl, etc, and more preferably phenyl resin.

The eluate to be used in the hydrophobic chromatography of the present invention may not be particularly limited, but preferably, a buffer solution having a pH of 6 to 8 comprising 0 to 1 M NaCl.

In the present invention, purification efficiency can be improved by diluting the anion-exchange resin eluate with a buffer solution having a pH of 6 to 8 comprising 3 to 4 M NaCl or by concentration/dialysis with a buffer solution having a pH of 6 to 8 comprising 1 to 3 M NaCl, prior to adsorbing the anion-exchange resin eluate to the hydrophobic resin, thereby increasing the concentration of NaCl in the anion-exchange resin eluate to 2 M or higher. Examples of the buffer solution to be used in the above respective washing and elution are preferably a sodium phosphate buffer solution, a potassium phosphate buffer solution, or a Tris buffer solution.

Additionally, it is preferred that the long-acting human growth hormone bound to the hydrophobic chromatography resin, which is obtained from loading the anion-exchange resin chromatography eluate to the hydrophobic chromatography resin, be eluted with a linear concentration gradient using the buffer solution.

Figure 6:
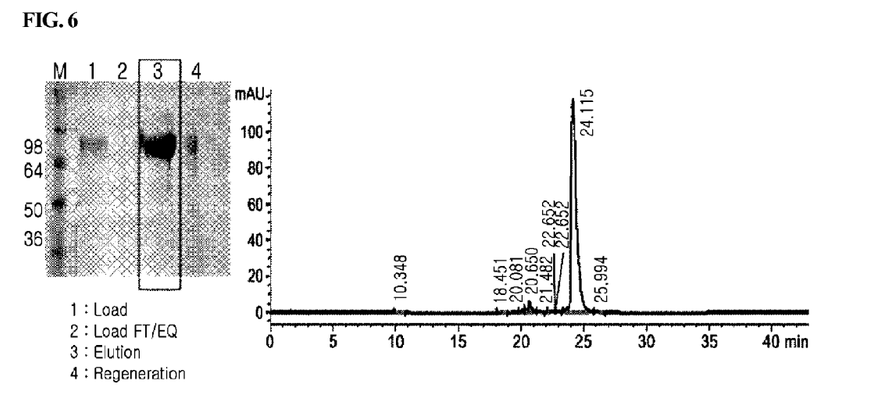
FIG. 6 shows a result of measuring the purity of a long-acting human growth hormone separated via hydrophobic resin chromatography and measured via SDS-PAGE and C4 HPLC analysis chromatography.

In an exemplary embodiment of the present invention, a long-acting human growth hormone was eluted by preparing a loading solution for phenyl-Sepharose by adding a 20 mM sodium phosphate buffer solution (pH 8.0) comprising 4 M NaCl to a Q-Sepharose column eluate to obtain a 20 mM sodium phosphate buffer solution (pH 8.0) comprising 2.5 M NaCl; loading the solution to the XK-50 column filled with phenyl-Sepharose equilibrated with a 20 mM sodium phosphate buffer solution (pH 8.0) comprising 2.5 M NaCl at a flow rate of 20 mL/min; washing with three column volumes of a 20 mM sodium phosphate buffer solution (pH 8.0) comprising 2.5 M NaCl; followed by eluting the long-acting human growth hormone with four column volumes of a 20 mM sodium phosphate buffer solution (pH 8.0) comprising 0.5 M NaCl. As a result, the purity of the obtained the long-acting human growth hormone was about 96% (FIG. 6).

Step (c) relates to the application of a biological fluid comprising the long-acting human growth hormone NexP-hGH or an eluate produced in step (a) or step (b) to affinity chromatography column filled with resin to which anti-alpha-1 antitrypsin antibody fragments are attached. Preferably, step (c) may relate to the addition of a culture broth comprising a long-acting human growth hormone NexP-hGH, an eluate produced in step (a) or step (b) to equilibrated affinity chromatography resin, to which anti-alpha-1 antitrypsin antibody fragments are attached, to be adsorbed thereto; washing with Tris buffer solution having a pH 6.5 to 8.5 comprising 0 to 200 mM NaCl; and eluting a fraction comprising the long-acting human growth hormone NexP-hGH by using Tris buffer solution having a pH of 6.5 to 8.5 comprising 0 to 1 M $MgCl_2$.

The importance of the high purification method of the present invention with high purity and high yield lies in that step (c), which relates to performing a process of resin to which antibody fragments are attached, is performed as a final step. The present inventors firstly confirmed that if culture broth, which contains a large amount of detergents, dyes, other impurities, etc., remaining in the diafiltered culture broth, is directly loaded to the chromatography process of step (c) as the first process, it is possible to obtain long-acting human growth hormone NexP-hGH with 90% or higher purity, however, it lowers binding capacity thereby decreasing yield.

The present inventors discovered that the process of firstly performing step (a) with high binding capacity (10 mg/mL or higher) on the long-acting human growth hormone NexP-hGH in the presence of detergents, dyes, and other impurities for partial removal of impurities, subsequently followed by step (b) and step (c) is a purification process to secure a purity of 98% or higher and a yield of 25% or higher, thereby completing the constitution feature of the present invention.

From the above anion-exchange resin and hydrophobic resin process, it is possible to obtain a long-acting human growth hormone NexP-hGH with 90 to 95% purity, and in order to obtain a long-acting human growth hormone NexP-hGH with 99% or higher purity a resin to which antibody fragments are attached may be further used. Additionally, it was confirmed that when the purification is performed using only the resin to which antibody fragments are attached the resulting yield decreases by about 20% compared to that of the above process but it is possible to obtain the long-acting human growth hormone NexP-hGH with a purity of about 90 to 95%.

Preferably, the eluate comprising the long-acting human growth hormone NexP-hGH obtained from the hydrophobic resin is concentrated and dialyzed with Tris buffer solution having a pH of 7 to 9 comprising 0 to 100 mM NaCl, or diluted so that the NaCl concentration in the solution becomes 200 mM or less. The concentrated and dialyzed solution or the diluted solution is adsorbed into resin to which antibody fragments are attached, in particular, the resin to which anti-alpha-1 antitrypsin antibody fragments are attached, washed with Tris buffer solution having a pH of 6.5 to 8.5 comprising 0 to 200 mM NaCl, and eluted with Tris buffer solution having a pH of 6.5 to 8.5 comprising 0 to 1 M $MgCl_2$.

Preferably, the buffer solution to be used in the respective washing and elution may be a sodium phosphate buffer solution, a potassium phosphate buffer solution, or a Tris buffer solution.

Figure 7:
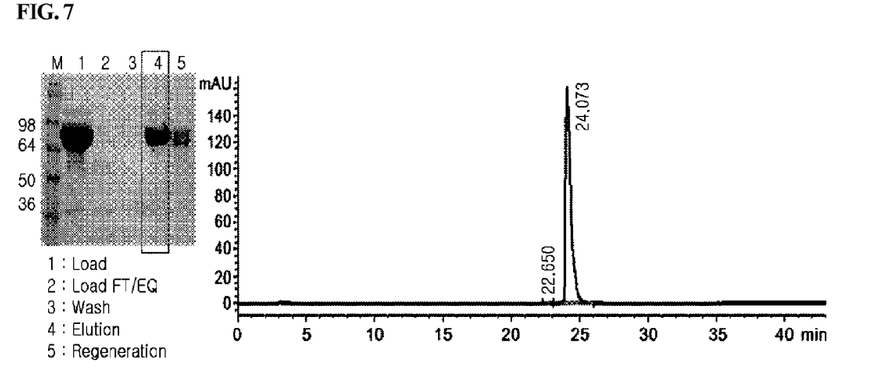
FIG. 7 shows a result of measuring the purity of a long-acting human growth hormone separated via affinity chromatography column filled with resin, to which anti-alpha-1 antitrypsin antibody fragments are attached, and measured via SDS-PAGE and C4 HPLC analysis chromatography.

In an exemplary embodiment of the present invention, the solution comprising the long-acting human growth hormone NexP-hGH obtained from step (b) was diafiltered via ultrafiltration system using Tris buffer solution (pH 7.4) comprising 150 mM NaCl. XK-50 column (GE Healthcare) filled with resin to which anti-alpha-1 antitrypsin (A1AT, hereinafter) antibody fragments are attached was equilibrated by allowing a sufficient amount of a Tris buffer solution (pH7.4) comprising 150 mM NaCl to flow into the column, and the diafiltered liquid was allowed to flow into the column at a flow rate of 20 mL/min, and again about three column volumes of Tris buffer solution (pH7.4) comprising 150 mM NaCl was again allowed to flow into the column to wash the same. Then, the column was washed with a Tris buffer solution (pH7.4) comprising 50 mM $MgCl_2$, and subsequently a Tris buffer solution (pH 7.4) comprising 100 mM $MgCl_2$, a Tris buffer solution (pH 7.4) comprising 200 mM $MgCl_2$ and a Tris buffer solution (pH 7.4) comprising 300 mM $MgCl_2$ were sequentially allowed to flow into the column to elute a fraction comprising the long-acting human growth hormone NexP-hGH. The eluate comprising the long-acting human growth hormone NexP-hGH was diafiltered via an ultrafiltration system (MWCO of 30,000) using a PBS buffer solution (pH 7.45) comprising 150 mM NaCl. The purity of the recovered eluate was shown to be about 99% (FIG. 7).

Preferably, the above method may further include step (d), in the purification step via affinity chromatography column filled with resin, to which anti-alpha-1 antitrypsin antibody fragments are attached, separating and eluting structural isoforms of the long-acting human growth hormone NexP-hGH with different glycan patterns and isoelectric points using 0 to 1,000 mM $MgCl_2$. Step (d) may use NaCl instead of $MgCl_2$, and preferably, the amount of NaCl used instead of $MgCl_2$ is 0 to 2000 mM, and may be a step for separating and eluting structural isoforms of the long-acting human growth hormone NexP-hGH with different glycan patterns and isoelectric points.

Figure 8:
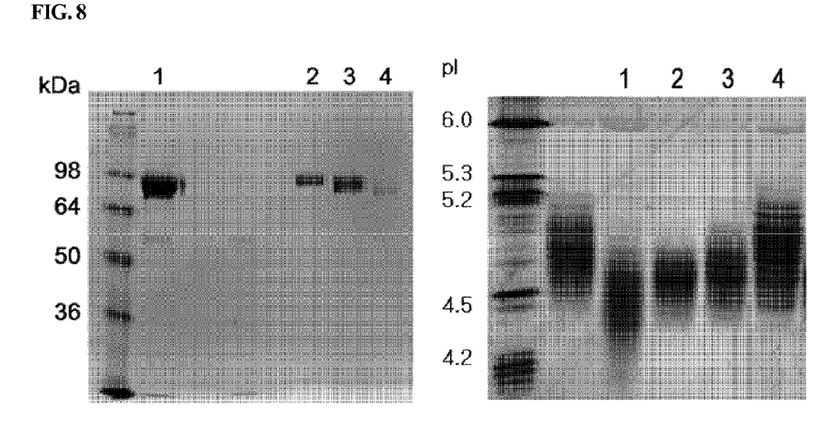

In separating the resin to which antibody fragments are attached, the isoforms of the long-acting human growth hormone NexP-hGH with different glycan patterns and isoelectric points may be separated and eluted according to the concentration of MgCl$_2$. For example, a 100 mM MgCl$_2$ buffer solution can selectively elute structural isoforms with more glycan patterns and lower isoelectric points than a 200 mM MgCl$_2$ buffer solution (FIG. 8).

The eluate obtained from the resin to which antibody fragments are attached comprising the long-acting human growth hormone NexP-hGH may be subject to a further buffer solution exchange process. The buffer solution exchange process may be performed via gel-filtration or concentration and diafiltration, etc.

In another aspect of the present invention, there is provided a long-acting human growth hormone NexP-hGH protein prepared by the above method. The method and the long-acting human growth hormone NexP-hGH protein are the same as explained above.

The highly glycosylated long-acting human growth hormone and a method of preparing the same according to the present invention exhibits a significant increase in glycosylation compared to the conventional human growth hormones, thus having a much improved long-acting property and pharmaceutical efficacy than the commercial human growth hormones in the market such as Diclase Inj.®, and thus can be useful in fields requiring human growth hormone.

Furthermore, the method of the present invention enables to obtain a recombinant long-acting human growth hormone NexP-hGH with a purity of 99% or higher from a cell culture using anion-exchange resin, hydrophobic resin, and resin to which antibody fragments are attached. The high purity purification method of the present invention, when applied to a manufacturing process, can purify long-acting human growth hormones in large scale to have high purity, and thus can be useful for the manufacture of protein therapeutic agents.

Hereinafter, the present invention will be described in more detail with reference to the following examples and experimental examples. However, the following examples and experimental examples are provided for illustrative purposes only, and the scope of the present invention should not be limited thereto in any manner. Those skilled in the art may appropriately select vectors and culturing conditions conventionally used according to the given circumstances.

Example 1: Preparation of a Human Growth Hormone/Alpha-1 Antitrypsin Fusion Protein and a Cell Line for Expression of the Fusion Protein A human growth hormone/alpha-1 antitrypsin fusion protein was cloned using pAV1, an improved vector derived from pSGHV0 (GenBank Accession No. AF285183) by removing shGH, His tag, and TEV sites therefrom, and was designed to enable an extracellular secretion using intrinsic signal sequences of proteins.

Additionally, DHFR system was introduced as a selective marker for the construction of a stable cell line for constitutive expression of the fusion protein, and for this purpose, IRES-DHFR gene was inserted into pAV1 vector. To increase the amount of expression, a Kozac sequence was additionally inserted into the signal sequence. The target protein, hGH-A1AT (Q9N, P357N), was introduced so that it can be fused with hGH at the N-terminus of A1AT.

The thus prepared clones were then introduced into CHO DG44 cell line, and selected up to 4 μM while allowing them to undergo a two-fold increase starting from 50 nM methotrexate (MTX), thereby establishing a stable cell line. However, those skilled in the art may appropriately select the conventionally used vectors and cell lines according to the given circumstances and apply them accordingly.

Experimental Example 1: Culturing a Cell Line Expressing a Long-Acting Human Growth Hormone/Alpha-1 Antitrypsin Fusion Protein and Production of the Fusion Protein In order to obtain the highly glycosylated growth hormone/alpha-1 antitrypsin fusion protein with high yield from the cell line established above, the growth hormone/alpha-1 antitrypsin fusion protein, i.e., the long-acting growth hormone of the present invention, was expressed in a conventional cell culture condition. However, those skilled in the art may appropriately select the conventionally used culture conditions according to the given circumstances and apply them accordingly.

Experimental Example 2: Fractionation of the Human Growth Hormone/Alpha-1 Antitrypsin Fusion Protein According to pI The expression cell line obtained from the Example above was subjected to suspension culture, and a novel long-acting growth hormone of the present invention obtained from the cell culture broth was purified. Specifically, the cell culture broth was filtrated to remove the cells, and thus the cell supernatant was obtained. The supernatant was diafiltered via ultrafiltration system (MWCO of 30,000) using an equilibrium buffer solution (20 mM sodium phosphate, pH 8.0). Then, the resultant was injected into a Q-Sepharose (GE Healthcare, USA) column, and removed protein impurities with a 20 mM sodium phosphate buffer solution (pH 8.0) comprising 50 mM NaCl, and allowed a 20 mM sodium phosphate solution (pH 8.0) comprising 190 mM NaCl to flow thereinto, and recovered a solution comprising a long-acting growth hormone.

A loading solution for phenyl-Sepharose (GE Healthcare, USA) was prepared by adding a 4 M NaCl/20 mM sodium phosphate buffer solution (pH 7.5) to a Q-Sepharose column eluate thereby adjusting the solution to about 2.5 M NaCl/20 mM sodium phosphate (pH 7.5). Then, the loading solution was loaded into a phenyl-Sepharose column and the column was washed with a 20 mM sodium phosphate buffer solution comprising 2.5 M NaCl. Subsequently, a solution comprising the long-acting human growth hormone was recovered using a 20 mM sodium phosphate buffer solution (pH 7.5).

The phenyl Sepharose column eluate was diafiltered via ultrafiltration system (MWCO of 30,000) using a Tris buffer solution (pH 7.4) comprising 150 mM NaCl. Then, the resultant was loaded into resin, to which anti-alpha-1 antitrypsin (A1AT) antibody fragments are attached, and bound thereto, and washed with a Tris buffer solution (pH 7.4) comprising 50 mM MgCl$_2$. Subsequently, a Tris buffer solution (pH 7.4) comprising 100 mM MgCl$_2$, a Tris buffer solution (pH 7.4) comprising 200 mM MgCl$_2$, and a Tris buffer solution (pH 7.4) comprising 300 mM MgCl$_2$ were sequentially allowed to flow thereinto, thereby fractionating and eluting the long-acting growth hormone of the present invention according to the difference in pI.

In particular, the long-acting growth hormones of the present invention eluted using a 100 mM MgCl$_2$/Tris buffer solution (pH 7.4), a 200 mM MgCl$_2$/Tris buffer solution (pH 7.4), and a 300 mM MgCl$_2$/Tris buffer solution (pH 7.4) were assigned as isoform 1, isoform 2, and isoform 3, respectively (FIGS. 1 and 2). Those skilled in the art may, in addition to the above methods, appropriately select conventional methods for protein separation according to isoelectric points.

Experimental Example 3: Pharmacodynamic Experiment on Human Growth Hormone/Alpha-1 Antitrypsin Fusion Protein In order to confirm the pharmacodynamics of fractionation of the long-acting growth hormone according to the present invention, an experiment was performed as follows. Hypophysectomized rats were administered with the above isoforms 1 to 3 via subcutaneous injection at a concentration of 0.6 mg/kg, and the change in their body weight and length were measured until the $14^{th}$ day, and the results are shown in FIGS. 3 and 4, respectively.

As a result, as shown in FIG. 3, the negative control group treated with PBS showed no change in body weight but the groups treated with isoforms 1 to 3 and the positive control group treated with Eutropin® and Declage® showed a significant increase of body weight. In particular, groups treated with isoform 1 and isoform 2 showed a distinct difference in body weight increase on the $10^{th}$ day compared to that of the positive control group, whereas the group treated with isoform 3 showed a lower increase in body weight than that of the positive control group.

Figure 4:
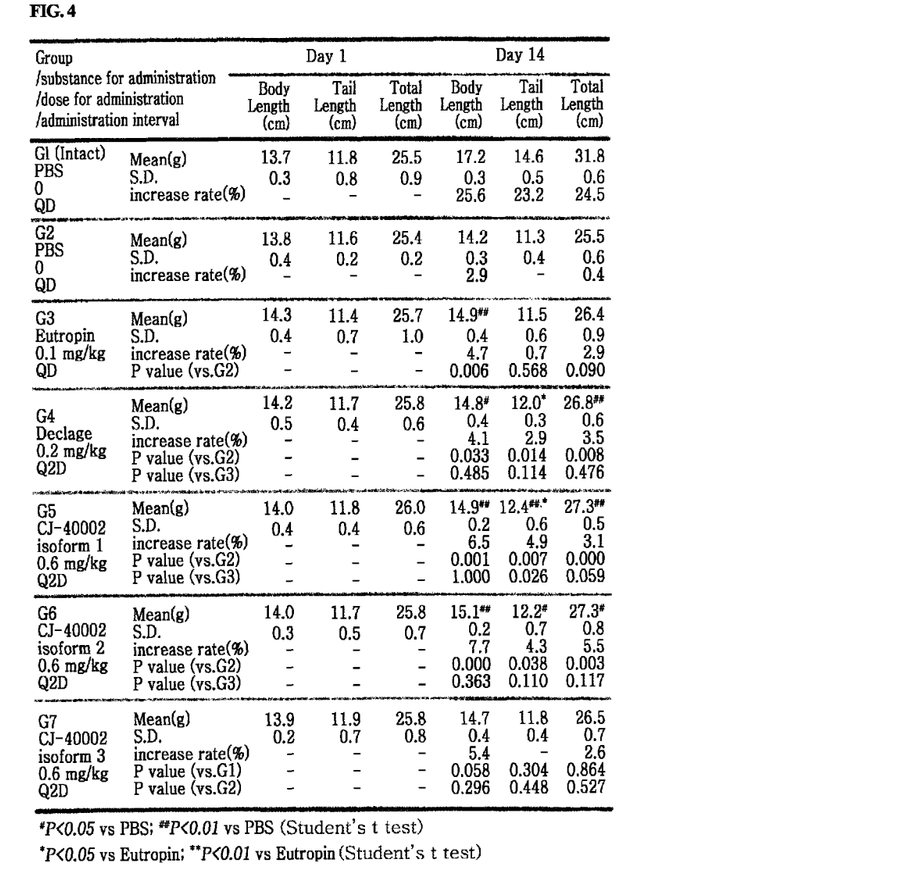
FIG. 4 shows a result of measuring the body length of isoforms 1 to 3 of the highly glycosylated long-acting human growth hormone of the present invention.

Additionally, the result of body length measurement revealed that groups treated with isoform 1 and isoform 2 showed a higher rate of body weight increase than that treated with Declage®, whereas the group treated with isoform 3 showed a little lower increase (FIG. 4). The above results suggest that even the same type of long-acting hormones may exhibit different efficacies depending on the degree of glycans, and in particular, may imply that the NexP-hGH protein manufactured according to the method of the present invention having a pI of 5.2 or less is a highly glycosylated protein, and has a long-acting property in vivo and a high growth effect.

Example 2: Method of Purifying Long-Acting Human Growth Hormone NexP-hGH Via Anion-Exchange Resin and Hydrophobic Resin Chromatography About 2 L of the culture broth obtained from the transformed CHO cells which expresses the long-acting human growth hormone NexP-hGH prepared in Example 1 was diafiltered via ultrafiltration system (MWCO of 30,000) using a 20 mM sodium phosphate buffer solution (pH 8.0).

XK-50 column (GE Healthcare) was filled with about 250 mL of Q-Sepharose (GE Healthcare) resin and equilibrated by allowing a sufficient amount of a 20 mM sodium phosphate buffer solution (pH 8.0) to flow thereinto. About 1 L of the diafiltered liquid was allowed to flow into the thus prepared Q-sepharose at a flow rate of 20 mL/min, and again the column was washed by allowing about 3 column volumes (CV) of a 20 mM sodium phosphate buffer solution (pH 8.0) to flow thereinto.

After removing protein impurities by allowing about 3 CV of a 20 mM sodium phosphate buffer solution (pH 8.0) comprising 100 mM NaCl to flow at a flow rate of 20 mL/min, about 3 CVs of a 20 mM sodium phosphate buffer solution (pH 8.0) comprising 200 mM NaCl was allowed to flow at a flow rate of 20 mL/min to recover a solution comprising the long-acting human growth hormone NexP-hGH.

The purity of the recovered eluate was measured via C4 HPLC analysis chromatography and the result is shown in FIG. 5. As a result, it was confirmed that the purity of the long-acting human growth hormone NexP-hGH was about 85%.

A phenyl-sepharose loading solution was prepared by adding 4 M NaCl/20 mM sodium phosphate buffer solution (pH 8.0) to a Q-Sepharose column eluate thereby adjusting the solution to about 2.5 M NaCl/20 mM sodium phosphate (pH 8.0). XK-50 column (GE Healthcare) was filled with about 250 mL of Q-Sepharose (GE Healthcare) resin and equilibrated by allowing a sufficient amount of a 20 mM sodium phosphate buffer solution (pH 7.5) comprising 2.5 M NaCl to flow thereinto. About 1.2 L of the phenyl-Sepharose loading solution was allowed to flow into the thus prepared phenyl-Sepharose column at a flow rate of 20 mL/min, and again the column was washed by allowing about 3 column volumes (CV) of a 20 mM sodium phosphate buffer solution (pH 8.0) comprising 2.5 M NaCl to flow thereinto.

A solution comprising the long-acting human growth hormone NexP-hGH was recovered by allowing about 4 CV of a 20 mM sodium phosphate buffer solution (pH 8.0) buffer solution comprising 0.5 M NaCl to flow at a flow rate of 20 mL/min.

The purity of the recovered eluate was measured via C4 HPLC analysis chromatography and the result is shown in FIG. 6. As a result, it was confirmed that the purity of the long-acting human growth hormone NexP-hGH was about 96%.

Example 3: Purification Method Using a Resin to which Anti-Alpha-1 Antitrypsin Antibody Fragments are Attached About 1 L of a solution comprising the long-acting human growth hormone NexP-hGH prepared in Example 2 was diafiltered via ultrafiltration system (MWCO of 30,000) using a Tris buffer solution (pH 7.4) comprising 150 mM NaCl XK-50 column (GE Healthcare) was filled with about 250 mL of resin, to which anti-alpha-1 antitrypsin antibody fragments are attached, (GE Healthcare) ("AIAT", hereinafter) and equilibrated by allowing a sufficient amount of a Tris buffer solution (pH 7.4) comprising 150 mM NaCl.

About 1 L of the diafiltered liquid was allowed to flow into the thus prepared A1AT column at a flow rate of 20 mL/min, and again the column was washed by allowing about 3 column volumes of a Tris buffer solution (pH 7.4) comprising 150 mM NaCl to flow thereinto. Then, the column was washed with a Tris buffer solution (pH 7.4) comprising 50 mM $MgCl_2$, and then allowed a Tris buffer solution (pH 7.4) comprising 100 mM $MgCl_2$, a Tris buffer solution (pH 7.4) comprising 200 mM $MgCl_2$, and a Tris buffer solution (pH 7.4) comprising 300 mM $MgCl_2$ to sequentially flow thereinto, thereby eluting a fraction comprising the long-acting human growth hormone NexP-hGH.

The eluate comprising the long-acting human growth hormone NexP-hGH was diafiltered via ultrafiltration system (MWCO of 30,000) using a PBS (pH 7.45) buffer solution comprising 150 mM NaCl.

The purity of the recovered eluate was measured via C4 HPLC analysis chromatography and the result is shown in FIG. 7. As a result, it was confirmed that the purity of the long-acting human growth hormone NexP-hGH was about 99%.

Example 4: Separation of Long-Acting Human Growth Hormone NexP-hGH According to Glycan Pattern and Isoelectric Point In Example 3, it was possible to separate and elute the structural isoforms of the long-acting human growth hormone NexP-hGH with different glycan patterns and isoelectric points according to the concentration of $MgCl_2$. The difference in glycan patterns and isoelectric points of the long-acting human growth hormone NexP-hGH separated and eluted using a Tris buffer solution (pH 7.4) comprising 100 mM $MgCl_2$, a Tris buffer solution (pH 7.4) comprising 200 mM $MgCl_2$, and a Tris buffer solution (pH 7.4) comprising 300 mM $MgCl_2$ are shown in FIG. 8.

The above results support that the long-acting human growth hormone of the present invention can be separated and purified with a purity of 99% or higher when the columns filled with anion-exchange resin, hydrophobic resin, and resin to which antibody fragments are attached to are sequentially used, and also the long-acting human growth hormone with a desirable glycosylation can be separated and purified according to the difference in glycosylation.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method of purifying a long-acting human growth hormone wherein the long-acting human growth hormone is a fusion protein of human growth hormone (hGH) and an alpha-1 antitrypsin mutant without protease inhibitor activity of the alpha-1 antitrypsin, the method comprising:
   (a) applying a biological fluid comprising the long-acting human growth hormone to anion-exchange resin chromatography;
   (b) applying the biological fluid comprising the long-acting human growth hormone or an eluate produced in step (a) to hydrophobic resin chromatography;
   (c) applying the biological fluid comprising the long-acting human growth hormone or an eluate produced in step (a) or step (b) to an affinity chromatography column filled with resin to which anti-alpha-1 antitrypsin antibody binding fragments are attached; and
   (d) separating and eluting structural isoforms of the long-acting human growth hormone with different glycan patterns and isoelectric points with 50 to 200 mM $MgCl_2$ in the purification process using the affinity chromatography column filled with resin, to which anti-alpha-1 antitrypsin antibody binding fragments are attached, wherein isoform 1 is eluted and collected from the affinity chromatography column at about 100 mM $MgCl_2$ and isoform 2 is eluted and collected from the affinity chromatography column at about 200 mM $MgCl_2$.

2. The method of claim 1, wherein step (a) is a step of adding a culture broth comprising a long-acting human growth hormone or diafiltered culture broth obtained by diafiltration of the culture broth with a buffer solution having a pH of 6 to 9 comprising 0 to 100 mM NaCl to equilibrated anion-exchange resin to be adsorbed thereto; washing the resin with a buffer solution having a pH of 6 to 9 comprising 0 to 100 mM NaCl; and eluting a fraction comprising the long-acting human growth hormone using a buffer solution having a pH of 6 to 9 comprising 100 to 1,000 mM NaCl.

3. The method according to claim 2, wherein the buffer solution used in washing or eluting is sodium phosphate buffer solution, potassium phosphate buffer solution, or Tris buffer solution.

4. The method of claim 1, wherein step (b) is a step of adding culture broth comprising a long-acting human growth hormone or a solution recovered from the anion-exchange resin chromatography to equilibrated hydrophobic resin to be adsorbed thereto; washing the resin with a buffer solution having a pH of 6 to 8 comprising 1 to 3 M NaCl; and eluting a fraction comprising the long-acting human growth hormone using a buffer solution having a pH of 6 to 8 comprising 0 to 1 M NaCl.

5. The method according to claim 4, wherein the buffer solution used in washing or eluting is sodium phosphate buffer solution, potassium phosphate buffer solution, or Tris buffer solution.

6. The method of claim 1, wherein step (c) is a step of adding culture broth comprising a long-acting human growth hormone or an eluate produced in step (a) or step (b) to equilibrated resin, to which anti-alpha-1 antitrypsin antibody binding fragments are attached, to be adsorbed thereto; and washing the resin with a buffer solution having a pH of 6.5 to 8.5 comprising 0 to 200 mM NaCl, and step (d) is a step of eluting a fraction comprising the long-acting human growth hormone with a buffer solution having a pH of 6.5 to 8.5 comprising 50 to 200 mM $MgCl_2$.

7. The method according to claim 6, wherein the buffer solution used in washing or eluting is sodium phosphate buffer solution, potassium phosphate buffer solution, or Tris buffer solution.

8. The method of claim 1, wherein the biological fluid is culture broth of animal cells.

9. The method of claim 1, wherein the functional group of the anion-exchange resin is any one selected from the group consisting of quaternary amine (Q), diethylaminoethyl (DEAE), and quaternary amino ethyl (QAE).

10. The method of claim 1, wherein the functional group of the hydrophobic resin chromatography is any one selected from the group consisting of phenyl, octyl, isopropyl, butyl, and ethyl.

* * * * *